United States Patent [19]
Brooks

[11] Patent Number: 4,864,234
[45] Date of Patent: Sep. 5, 1989

[54] TRANSDUCERS AND METHOD FOR MAKING SAME

[75] Inventor: Robert A. Brooks, Rye, N.Y.

[73] Assignee: Magnetic Analysis Corporation, Mount Vernon, N.Y.

[21] Appl. No.: 191,683

[22] Filed: May 9, 1988

[51] Int. Cl.$^4$ ............................................. G01N 27/82
[52] U.S. Cl. ................................... 324/228; 324/237; 324/238; 336/20; 336/225
[58] Field of Search ............... 324/228, 234, 236, 237, 324/238, 239, 240; 336/225, 65, 20, 196, 199, 208, 221

[56] References Cited

U.S. PATENT DOCUMENTS 3,594,670  7/1971  Weigel .................................. 336/20
4,203,069  5/1980  Davis ............................ 324/228 X
4,516,103  5/1985  Arnold ................................. 336/65

Primary Examiner—Reinhard J. Eisenzopf
Assistant Examiner—Robert W. Mueller
Attorney, Agent, or Firm—Robin, Blecker, Daley & Driscoll

[57] ABSTRACT

A transducer for object examination comprises a conductive member of generally disc-shape having an opening of generally triangular configuration extending from the periphery of the member toward its center with opposed sidewalls of the opening in nonparallel relation to one another. A winding is applied to the perimeter of the conductive member and spans the opening. In certain instances, the transducer winding defines successive courses in each turn thereof which are of respective different diameter.

23 Claims, 6 Drawing Sheets

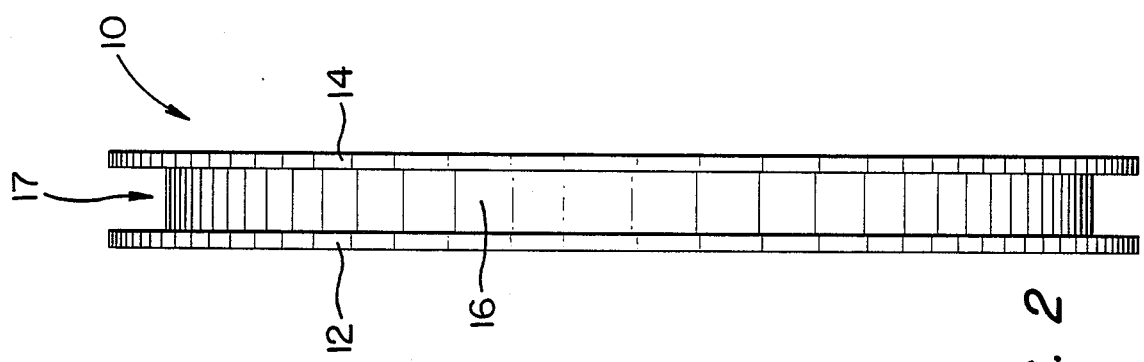
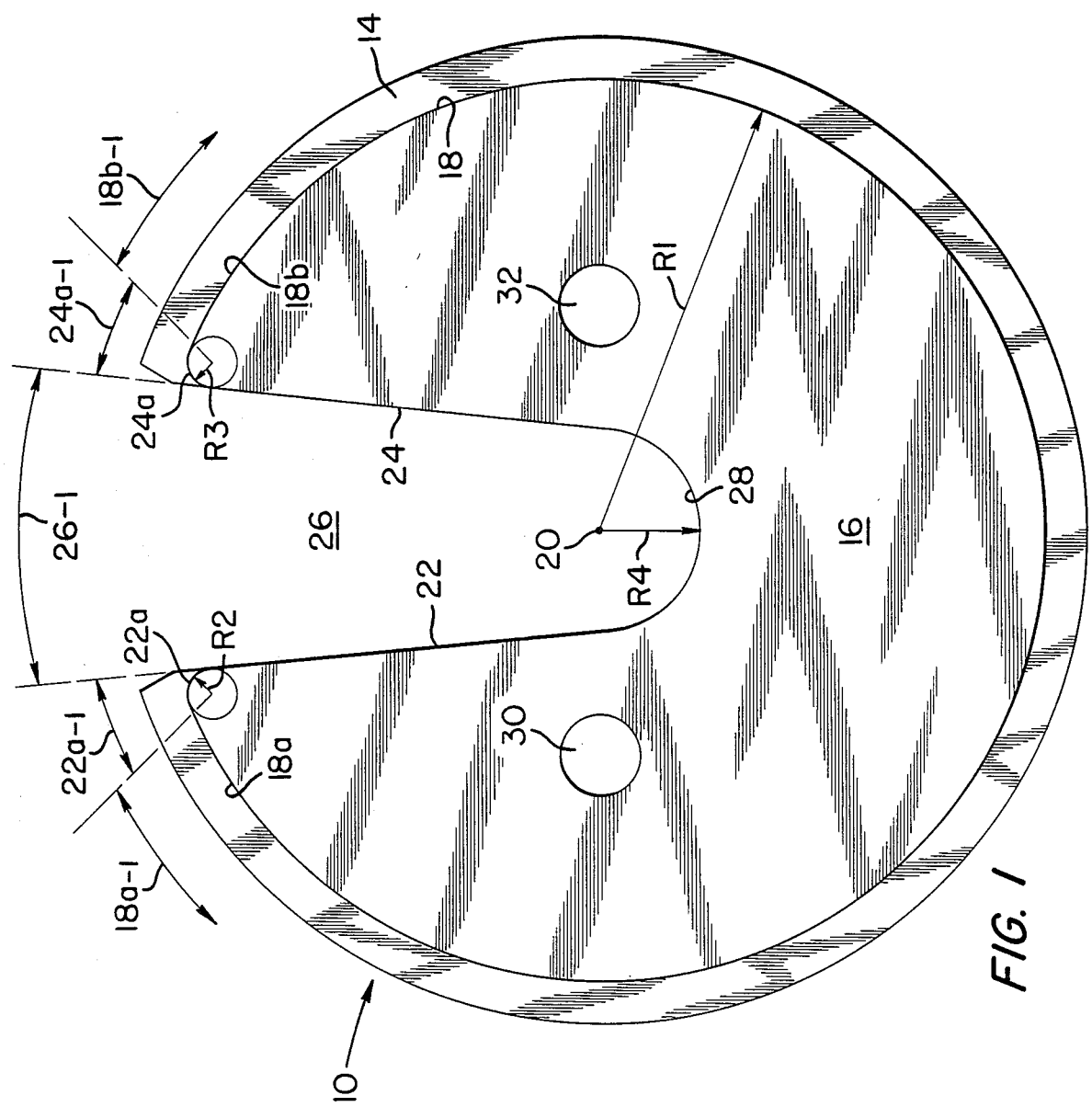

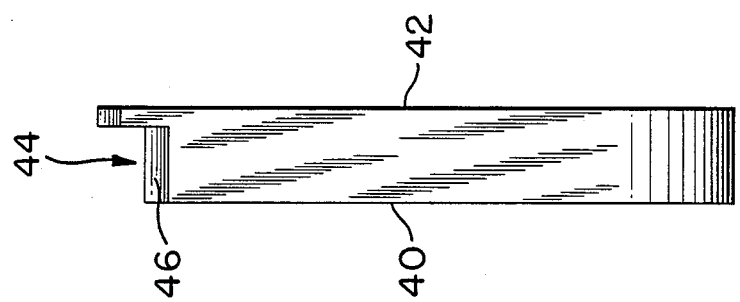
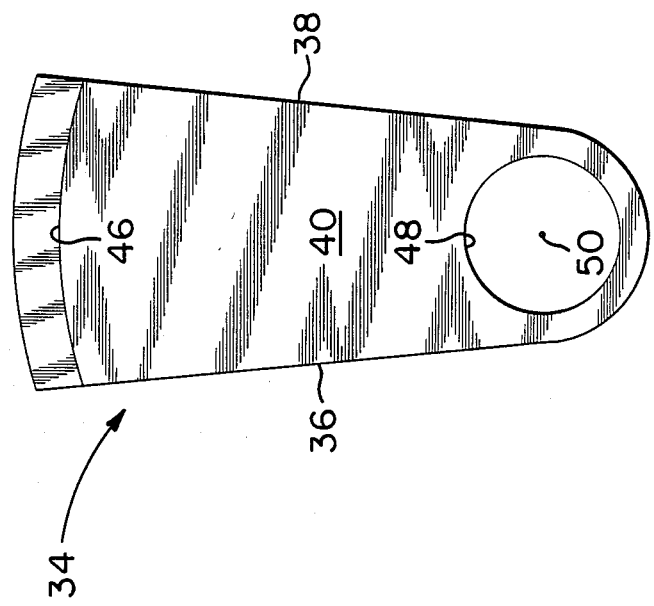
FIG. 4
FIG. 3

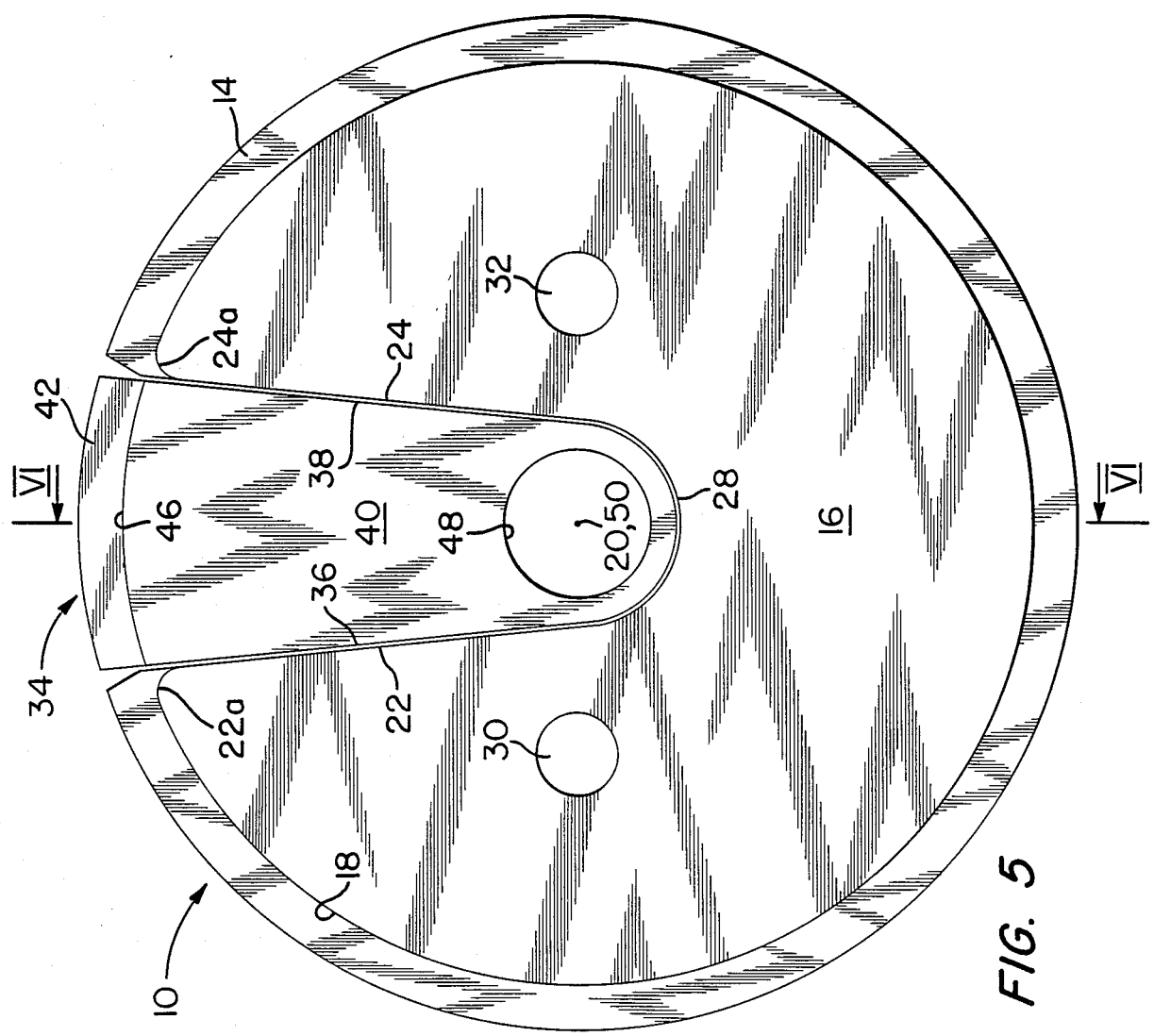

TRANSDUCERS AND METHOD FOR MAKING SAME

FIELD OF THE INVENTION

This invention relates generally to nondestructive object examination and pertains more particularly to improved transducers for use in such examination and to methods for making such transducers.

BACKGROUND OF THE INVENTION

U. S. Pat. Nos. 3,872,379 and 3,887,865, which are commonly assigned herewith, disclose transducers of so-called "monoturn" type for magnetic detection of object flaws. A disc-shaped conductive member is therein provided with an interior central aperture, for passage of a test object through the transducer, and a slot extends radially from the central aperture to the periphery of the disc-shaped member. A coil encircles the disc-shaped member and alternating or pulsed current supplied thereto produces current flow around the inner surface of the central aperture, thereby providing a cyclic, magnetic field which induces eddy currents in the test object. The term "monoturn" is derived from the single turn surface of the disc-shaped member about the central opening.

Considering the energized coil as a primary winding, a secondary winding is applied to the disc-shaped member to generate output signals indicative of test object eddy current characteristics. The secondary winding output signals serve to identify flaws present in the test object evidenced by cognizable departures of such current characteristics from those which are known to identify a flawless standard specimen. The secondary winding can also serve both functions, in which the primary winding is not necessary.

A characteristic of the monoturn, discussed in the '379 patent as follows, is that, for an encircling primary coil of given diameter and ampere turns, a considerable increase in flux density can be obtained in the aperture as the aperture diameter is decreased. A related advantage is that the inductance of the primary coil is lessened over that obtained in other transducers since such inductance is more a function of the cross-sectional area of the aperture, in which the flux is concentrated, than of the diameter of the winding constituting the primary coil.

The monoturn structures of the referenced patents of applicant are of object-encircling type. Offsetting the above advantages, convenience of usage thereof, as against usage of so-called "tangent coils", is accordingly limited. In this connection, tangent coils, not of monoturn type, have heretofore been used in magnetic object examination and have various usage advantages. One advantage is mechanical in that the tangent coil need only access a peripheral portion of the test object, providing simplicity both in coil and coil support structure. A second advantage is operational and relates to signal-to-noise improvement over encircling coils. Thus, considering the weld zone of a welded steel tube, for example, the major noise source is not the weld area, but the remnant, unwelded area of the tube. Use of a tangent coil in registry with the weld area, as against use of an encircling coil, would accordingly enhance signal-to-noise ratio.

Difficulty arises, however, in conforming a tangent coil to the surface of a portion of a test object. Surface conformity, from applicant's viewpoint, is a prerequisite for proper flaw examination. While considered by applicant, the use of a monoturn coil, as heretofore known, as a tangent coil would be ineffective, since it would be lacking in such surface conformity with a portion of a test object, except in the very narrow slot of the conductive member.

SUMMARY OF THE INVENTION

The primary object of the present invention is the provision of improved transducers for nondestructive, magnetic object examination.

A more particular object of the invention is to provide transducers enjoying the aforementioned advantages of both such known monoturn and tangent coil transducers.

A specific object of the invention is to facilitate the testing of concave, convex or otherwise configured surfaces in test objects.

In the attainment of these and other objects, the invention, in broad sense, inverts the flux concentration of the known monoturn transducer, from centrally therein, to radially exteriorly in transducers of the invention. Further, while disposing the test object in the path of such concentrated flux, transducers of the invention provide a tangent coil both in such flux concentration path and in surface conformity with the test object.

In realizing such broad sense function, the invention provides a transducer for object examination, akin to the known monoturn transducer in comprising a conductive member generally of disc shape and having a radial opening extending from a prescribed peripheral sector of the member toward its center. Unlike the known monoturn transducer, which defines a radially extending slot of generally rectangular configuration, transducers of the invention have slots of generally triangular configuration, which are better described as openings, with diverse result discussed hereinafter. The opposed sidewalls of the opening are in nonparallel relation to one another and terminating in a generally open interior member portion of partial circular outline. Further akin to the known monoturn transducer, transducers of the invention have a perimetric coil, but the extent thereof not supported by the disc-shaped member is longer, given the nature of the slots of transducers of the invention. Finally, akin to the tangent coil, transducers herein have exterior coil extent in surface conformity with an object to be tested, but exhibit ready surface conformance in this respect which may be convex, concave or otherwise configured and is disposed in registry with the concentrated flux issuing from the opening.

In otherwise viewing transducers in accordance with the invention, their conductive, disc-shaped members may be of the same or different radius than the object being tested. In the latter case, the winding will have first and second successive courses in each turn thereof which are of respective different radii. The first course is on the periphery of the conductive member and has the radius of the disc-shaped member. The second course spans the opening and will have a radius dictated by the size selected for the opening.

In methods for making transducers hereof, a first step involves configuring an electrically conductive member in disc-like shape and forming a generally triangularly shaped opening extending inwardly from the member periphery. In a second step, one configures an insert member in shape to be insertable in such opening and therein to be supplemental to the disc-shaped member, i.e., to provide a full perimeter for the composite assembly of disc-shaped member and insert. A third step involves the insertion of the insert member in such opening and applying a winding to the assembly.

In the described method, where the end usage intent is for the testing of an object by relating to a convex surface or otherwise configured to the periphery thereof, the insert can be of any composition and is removed in a step succeeding the assembly as described. The coil is then bowed into the opening to be in surface conformity with the object, based on the selection of opening size, again as described hereinafter.

In the described method, where the end usage intent is for the testing of an object by relating to a concave or otherwise configured interior thereof, the insert is of electrically nonconductive composition and remains with the assembly during usage, maintaining the coil in assembled, circularly supplemental relation with the disc-shaped member. As such, the coil is again in surface conformity with the object, based on the selection of opening size.

In a particularly preferred transducer embodiment in accordance with the invention, a conductive member has a boundary surface in first part configured with a first surface concentric with a center of the member and in second part by second surfaces extending from the member first surface and mutually nonparallel, each such second surface having a circular end segment continuous with the first surface. A winding is disposed about the first surface and spanning such second surface circular end segments.

The foregoing and other objects and features of the invention will be further understood from the following detailed discussion of preferred embodiments thereof and from the drawings wherein like reference numerals identify like components and parts throughout.

DESCRIPTION OF THE DRAWINGS

FIG. 1 is a front elevation of a disc-shaped conductive member in accordance with the invention with its forward wall omitted to show interior detail.

FIG. 2 is a side elevation of the conductive member of FIG. 1 with such forward wall shown in place.

FIG. 3 is a front plan elevation of an insert for the conductive member of FIG. 1.

FIG. 4 is a side elevation of the insert of FIG. 3.

FIG. 5 is a front elevation of the subassembly of the conductive member of FIG. 1 and the insert of FIG. 3, again with the forward wall of the conductive member omitted.

FIG. 6 is a sectional view of the subassembly of FIG. 5 as would be seen from plane VI—VI of FIG. 5, with the forward wall in place.

DESCRIPTION OF THE PREFERRED EMBODIMENTS

Figure 7:
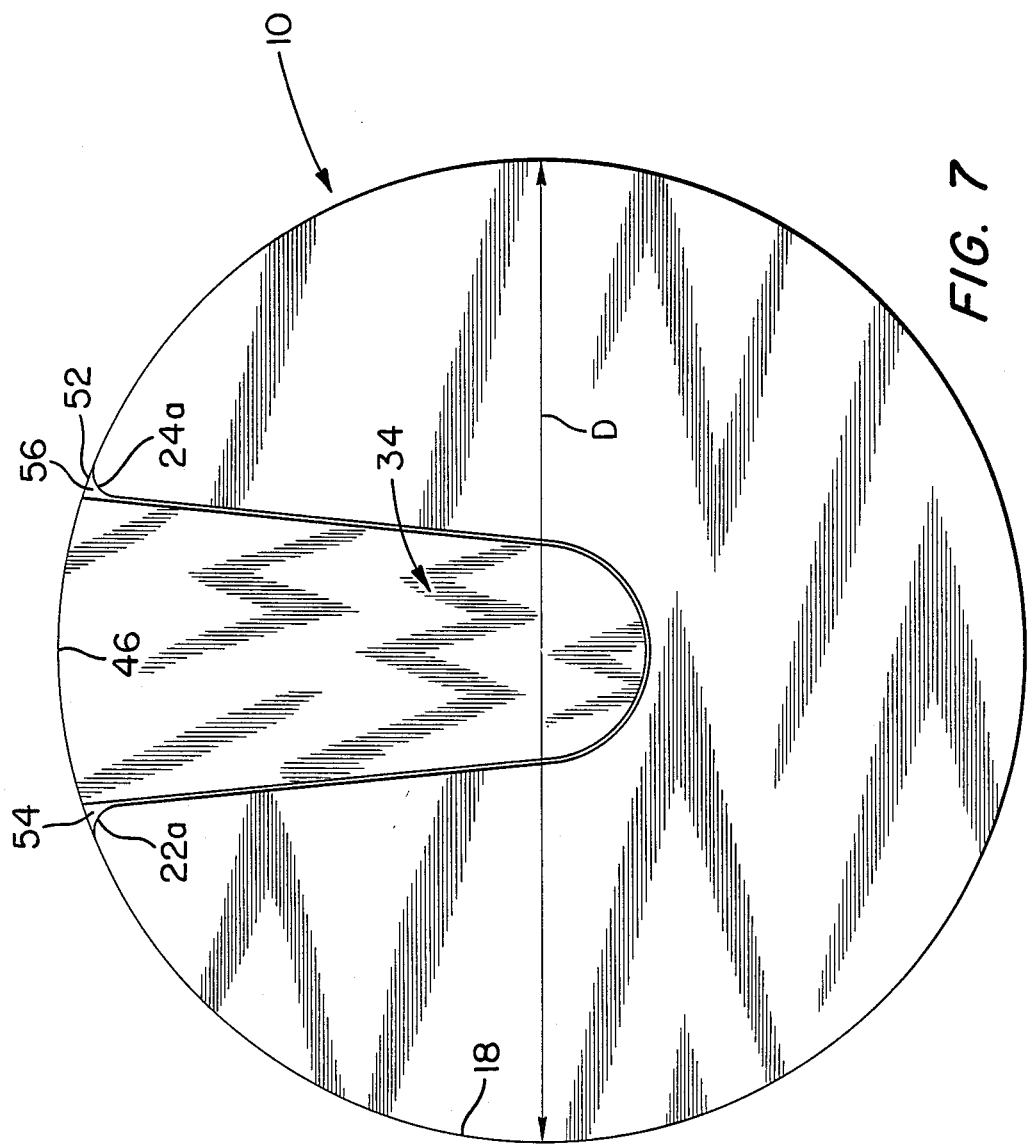
FIG. 7 is a schematic showing of FIG. 5, with both the forward and rearward walls of the conductive member omitted and having a winding assembled therewith.

Referring to FIGS. 1 and 2, a first structural element of a transducer in accordance with the invention comprises disc-shaped member 10 comprised of electrically conductive material, which has forward wall 12, rearward wall 14 and center body portion 16, all preferably integrally formed of a common material. A radially open recess 17 is formed between walls 12 and 14 onto the periphery of center body portion 16. Member 10 has a boundary surface in first part configured with a surface 18, concentric with the center 20 of member 10 at radius R1 and continuous between end extents 18a and 18b, which have courses 18a-1 and 18b-1, and in second part by surfaces 22 and 24, extending generally radially of the member surface 18. Surfaces 22 and 24 have respective end segments 22a and 24a, having courses 22a-1 and 24a-1, formed essentially as semicircles of equal radii R2 and R3, and continuous with surface extents 18a and 18b and surfaces 22 and 24.

Surfaces 22 and 24 are mutually spaced to define opening 26, the course of which is indicated at 26-1. The boundary surface of member 10 is completed by surface 28, formed concentrically with center 20 at radius R4. Passages 30 and 32 are provided through member 10 for assembling it with a housing (not shown).

Referring to FIGS. 3 and 4, an insert 34 is complemental to surfaces 22, 24 and 28 of opening 26 of FIG. 1, including counterpart surfaces 36, 38 and 40. Forward wall 40 is of lesser length than insert rear wall 42 and a frontally open nest 44 is thus formed atop insert circular surface 46. Opening 48 is provided interiorly of surface 40 and surface 46 is formed at radius R1 (FIG. 1) with respect to the center 50 of opening 48 to be circularly supplemental, upon insertion in the disc-shaped member, to form a circular perimeter therewith.

Insert 34 is shown in assembly with member 10 in FIGS. 5 and 6. As is seen, surface 46 of insert 34 is at common radius with surface 18 of member 10 and the insert rear wall 42 is at common radius with rear wall 14 of member 10. Centers 20 and 50 coincide. In FIG. 6, insert 34 is shown as being comprised of a synthetic material and member 10 is shown as an integral body of metal and the different cross-hatchings show more specifically the manner of the complemental relation therebetween in assembly.

Turning to the schematic showing of FIG. 7, a winding 52 is shown applied to the assembly of member 10 and insert 34. The initial turn of the winding will be seen to be of length equal to the perimeter of the assembly, namely, pi (3.1417) times the diameter D of member 10. Further, it will be observed that winding 52 is contiguous with surface 18 of member 10 and with surface 46 of insert 34 and otherwise bridges or spans the spacings 54 and 56 between end segments 22a and 24a and insert 34 without contiguity to the assembly.

Figure 8:
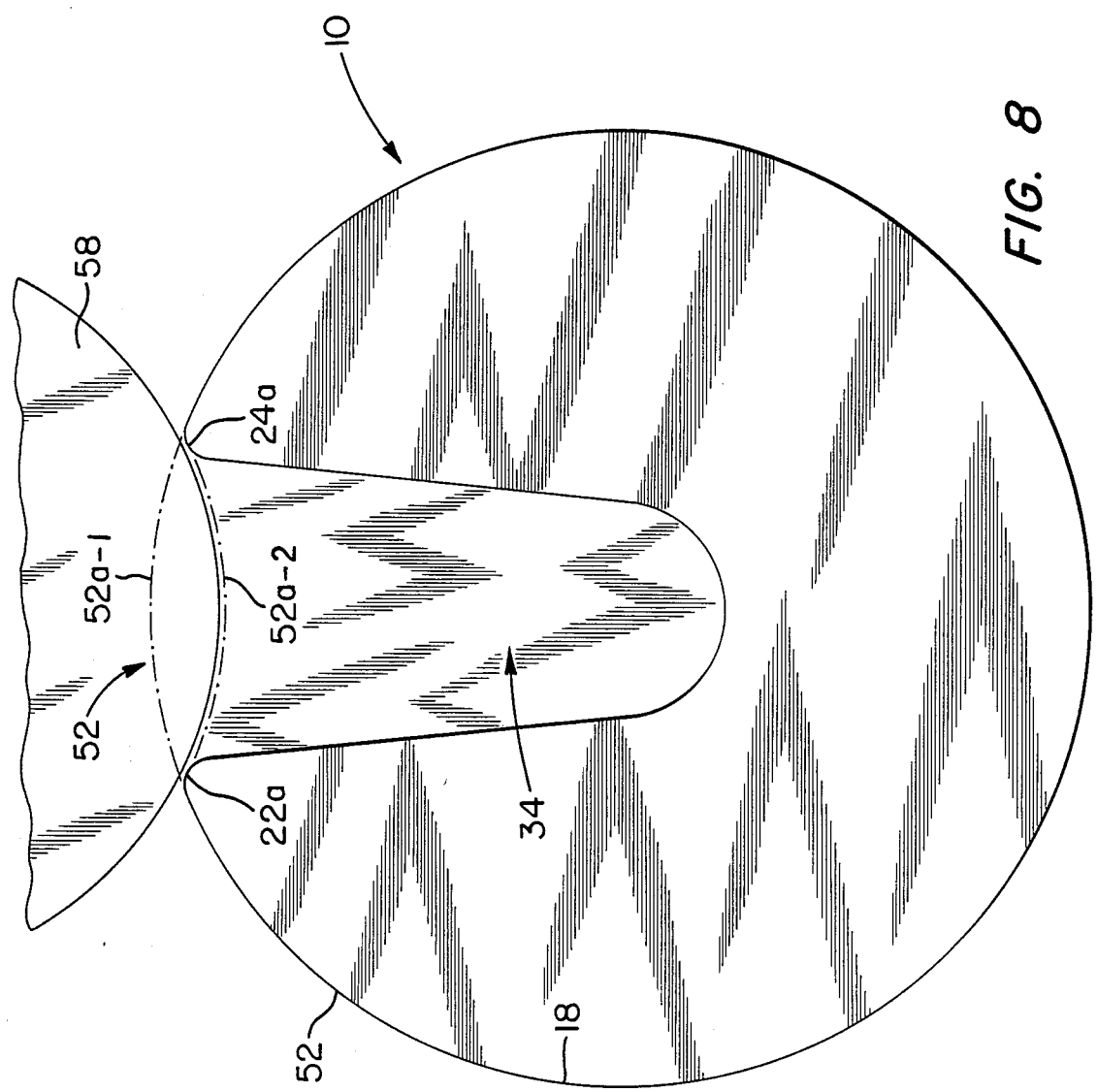
FIG. 8 is a further schematic showing from FIG. 7, wherein the insert of FIG. 3 is removed from the subassembly, and including a showing of a test object and the winding in phantom with the winding in both unbowed and bowed state.

In usage of the described transducer for examining the exterior convex surface of a test object, upon completion of application of winding 52 to the FIG. 7 assembly, insert 34 is removed therefrom. This is permitted since forward wall 40 of insert 34 is foreshortened radially as in FIG. 4 to form open nest 44, as above discussed. The schematic showing of FIG. 8 illustrates this condition with a winding portion 52a in disposition 52a-1, bridging opening 26 of member 10 at radius R1. Winding portion 52a is now bowed radially interiorly of member 10 to assume the disposition 52a-2 thereof. Radii R2 and R3, which are equal, are selected such that the winding portion 52a is tangential in its 52a-2 disposition, as it is in its 52a-1 disposition with respect to the periphery 18 of member 10. Accordingly, such interiorly bowed winding portion 52a, in its 52a-2 disposition will likewise be tangential throughout its extent when in operative relationship with a test object, as shown at 58 in FIG. 8.

In the transducer depicted in FIGS. 1-8 and discussed to this juncture, the diameter thereof is equal to that of the test object. This embodiment will be appreciated as illustrative of that particular transducer-object relation. However, the test object need not necessarily have the same diameter as the transducer, as is now shown with respect to FIG. 9.

Figure 9:
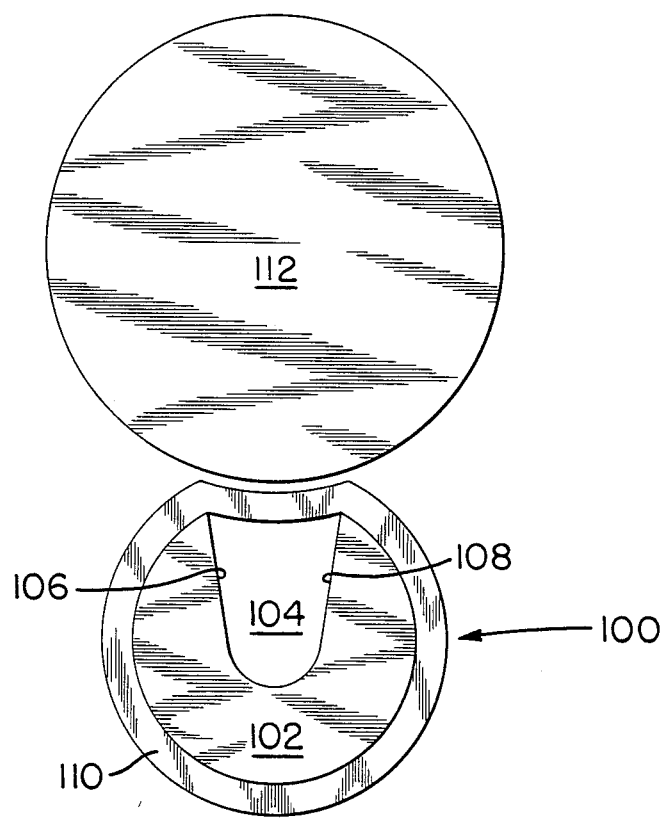
FIG. 9 is a schematic showing which depicts a concave test coil transducer arrangement for the testing of the exterior of an object wherein the disc-shaped member of the transducer is of diameter less then the diameter of the test object.

In FIG. 9, transducer 100 has conductive member 102 with opening 104 extending to the periphery of member 102 and bounded by sidewalls 106 and 108. Winding 110 is wrapped about the periphery of member 102, with an insert (removed in the FIG. 9 showing) situated in opening 104, in manner above discussed. Transducer 100 is shown in disposition examining the exterior surface of test object 112, with the portion of winding 110 spanning opening 104 confronting the test object periphery through an air gap.

As is seen in this embodiment, although the transducer has a smaller diameter than the test object, selection of the geometry of opening 104 and the locations of the radially outward ends of sidewalls 106 and 108 enable winding 110 to be in surface conformity with the object perimeter. Thus, winding 110 can be viewed as having successive courses at different radii, the course spanning opening 104 having the test object radius and the course upon the surface of conductive member having the radius thereof.

Figure 10:
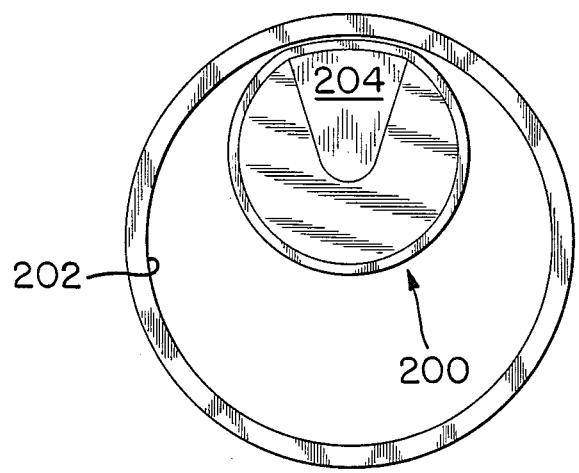
FIG. 10 is a schematic showing which depicts a convex test coil transducer arrangement for the testing of the inner surface of a test object, the transducer disc-shaped member being of diameter less than the diameter of the test object interior.

A like diverse radii transducer 200 is seen in FIG. 10 with a convex winding course in testing relation to the interior wall 202 of a test object. In this instance, insert 204 is retained with the transducer assembly in use thereof, serving to maintain surface conformity of the winding with the test object. In this case, the insert is selected to be of electrically nonconductive material, whereas its composition is not of consequence in the application of FIGS. 1-8 or the application of FIG. 9, since the insert is removed from the transducer in adapting same for use.

The above discussed characteristic of known monoturn transducers, wherein flux density is increased upon aperture size reduction, applies likewise in the transducers of the invention, wherein the opening, such as 104 of FIG. 9, corresponds to the combined slot and central aperture of the known monoturn for this purpose. In this context, lessening the size of opening 104 from that shown in FIG. 9 will increase flux density issuing from the transducer. Inductance likewise is more a function of the cross-sectional area of the opening rather than the diameter of the winding. Plural or single coils are also applicable to the transducers of the invention. In a further advantageous characteristic which transducers of the invention share with the known monoturn transducers of the cited patents of applicant, flux concentration in the opening herein is heightened by virtue of the fact that flux measurement about the transducer, except in the opening, indicates that there is little or no flux leakage about the transducer in areas not involved in confrontation with test objects.

Various changes may be introduced to the foregoing structure of the preferred embodiment and modifications may be introduced in the foregoing method of manufacture without departing from the invention. The particularly described and depicted preferred embodiments and practices are accordingly intended in an illustrative and not in a limiting sense. The true spirit and scope of the invention is set forth in the appended claims.

What is claimed is:

1. A transducer for examination of an object by juxtaposition with a surface of said object of predetermined configuration, said transducer comprising a conductive member of generally disc-shape having an opening of generally triangular configuration extending from the periphery of said member toward its center, opposed sidewalls of said opening being in nonparallel relation to one another, and a winding disposed at the perimeter of said conductive member and spanning said opening, said winding extent spanning said opening being adapted for juxtaposition with said object surface of said predetermined configuration.

2. The transducer claimed in claim 1 wherein said winding includes firs and second mutually successive courses in each turn thereof having respective different radii.

3. The transducer claimed in claim 2 wherein said winding first course is disposed on said conductive member and wherein said winding second course is in spanning relation to said opening.

4. The transducer claimed in claim 3 wherein said winding second course is in concave relation to said opening.

5. The transducer claimed in claim 3 wherein said winding second course is in convex relation to said opening.

6. The transducer claimed in claim 1 wherein said sidewalls of said opening terminate in a generally open interior portion of said member of partial circular configuration.

7. The transducer claimed in claim 6 wherein said member open interior portion partially encircles the center of said member.

8. A transducer for of an object by juxtaposition with a surface of said object of predetermined circular configuration, said transducer comprising a conductive member of generally disc-shape having an opening extending from the periphery of said member and a winding disposed on said member periphery, said winding including first and second mutually successive courses in each turn thereof having respective different radii, said winding second course radius corresponding to that of said object surface of said predetermined circular configuration.

9. The transducer claimed in claim 8 wherein said winding first course is disposed on said conductive member and wherein said winding second course is in spanning relation to said opening.

10. The transducer claimed in claim 9 wherein said winding second course is in concave relation to said opening.

11. The transducer claimed in claim 9 wherein said winding second course is in convex relation to said opening.

12. A method for making a transducer for object examination, comprising the steps of:
   (a) configuring an electrically conductive member generally in disc-shape and forming a generally triangular opening therein extending inwardly from the member periphery;
   (b) configuring an insert member in shape to be insertable in such opening and to be circumferentially supplemental to said member periphery when inserted therein; and
   (c) assembling said insert member in said conductive member and applying a winding about directly upon the periphery of such assembly.

13. The method claimed in claim 12 including the further step of removing said insert member from said conductive member following such application of said winding to said assembly.

14. The method claimed in claim 13 including the further step of displacing said winding in part into said member opening.

15. The method claimed in claim 12 wherein said insert member is selected to be of electrically nonconductive material and wherein said insert member is retained in said assembly to be present on usage of said transducer.

16. The method claimed in claim 12 wherein said opening is dimensioned to provide for successive first and second courses in each turn of said winding which are of respective different radii.

17. In combination, for the making of a transducer for use in object examination:
   (a) a member of conductive material, said member having a bounding surface configured in first part by a first surface concentric at a preselected radius with a center of said member and configured in second part by second surfaces extending into said member from said first surface and mutually spaced to define an opening extending interiorly of said first surface and
   (b) an insert complemental with said member for releasable disposition in said opening, said insert defining a peripheral surface portion supplemental with said first surface of said member on such disposition of said insert in said opening,
   said member further including means for retaining with said transducer a winding applied to said first surface.

18. The combination claimed in claim 17 wherein said member second part bounding surface further includes a third surface concentric with said first surface and continuous with said second surfaces.

19. The combination claimed in claim 17 further including a forward wall and a rear wall for said member, said opening extending into each of said forward wall and said rear wall.

20. The combination claimed in claim 19 wherein said forward wall and said rear wall are formed in common diameter greater than said member diameter, a radially open recess thereby existing between said forward and rear wall onto said bounding surface of said member, said insert having a rear wall for registry with said member rear wall on such disposition of said insert in said opening.

21. A method for the making of a transducer for use in object examination, comprising the steps of:
   (a) forming a conductive member generally in disc shape, with an opening extending radially interiorly from a portion of its periphery and configuring the radially exterior ends of such opening in circular manner;
   (b) forming an insert for disposition in said conductive member to have dimensions complemental to those of said opening and to have a peripheral part continuous circularly with and thus complemental to the periphery of the conductive member;
   (c) disposing said insert in said opening to provide an assembly of said conductive member and said insert;
   (d) applying a winding to such assembly in contiguous relation with said member periphery and said insert peripheral part to form a further assembly; and
   (e) removing said insert from said further assembly.

22. The method claimed in claim 21 including the further step of displacing said winding into said opening.

23. A kit of components for use in the making of a plurality of transducers for the respective examination of diversely sized objects, comprising:
   (a) a plurality of differently-sized members of conductive material, said members having respective individual bounding surfaces configured in first part by a first surface concentric at a preselected radius with a center of said member and configured in second part by second surfaces extending generally radially of said member first surface and mutually spaced to define an opening extending interiorly of said first surface, each said second surface having a circular end segment continuous with said first surface, each such preselected radius for said members corresponding to the radius of one of said diversely sized objects; and
   (b) a plurality of inserts each complemental with a different one of said members for releasable disposition in said opening thereof and defining a peripheral surface portion having a selective one of such preselected radii and for registry with said first surface of its corresponding member on such disposition of said insert in said opening.

* * * * *